(12) United States Patent
Arrieta et al.

(10) Patent No.: US 11,331,460 B1
(45) Date of Patent: *May 17, 2022

(54) DILATOR DEVICE

(71) Applicant: Dalent, LLC, Coral Gables, FL (US)

(72) Inventors: Agustin Arrieta, Pinecrest, FL (US); Peter Flores, Miami, FL (US); Felipe Echeverri, Coral Gables, FL (US)

(73) Assignee: Dalent, LLC, Coral Gables, FL (US)

( * ) Notice: Subject to any disclaimer, the term of this patent is extended or adjusted under 35 U.S.C. 154(b) by 323 days.

This patent is subject to a terminal disclaimer.

(21) Appl. No.: 16/421,351

(22) Filed: May 23, 2019

Related U.S. Application Data

(63) Continuation of application No. 15/635,666, filed on Jun. 28, 2017, now Pat. No. 10,322,269, which is a
(Continued)

(51) Int. Cl.
*A61B 17/24* (2006.01)
*A61M 29/02* (2006.01)
*A61M 1/00* (2006.01)

(52) U.S. Cl.
CPC ............ *A61M 29/02* (2013.01); *A61M 1/774* (2021.05); *A61M 2210/0618* (2013.01)

(58) Field of Classification Search
CPC .............. A61B 17/24; A61B 17/12104; A61B 17/12136; A61B 17/0057;
(Continued)

(56) References Cited

U.S. PATENT DOCUMENTS

| 705,346 A | 7/1902 | Hamilton |
|---|---|---|
| 1,735,519 A | 11/1929 | Vance |

(Continued)

FOREIGN PATENT DOCUMENTS

| WO | WO 2013/179217 | 12/2013 |
|---|---|---|
| WO | WO 2017/000582 | 1/2017 |

(Continued)

OTHER PUBLICATIONS

Gottmann, et al., Balloon Dilatation of Recurrent Ostial Occlusion of the Frontal Sinus, CIRSE Abstract and Presentation (Mar. 2001) B-04353.
(Continued)

*Primary Examiner* — Vi X Nguyen
(74) *Attorney, Agent, or Firm* — Knobbe Martens Olson & Bear, LLP

(57) ABSTRACT

A dilator device including an elongated flexible material sleeve having a hollow interior extending along a distal portion and a proximal portion thereof. An expandable or inflatable bladder is connected to the distal portion and disposable radially outward from an exterior of the sleeve when in an expanded and/or inflated orientation. The elongated sleeve including a tip having a predetermined configuration that facilitates positioning the elongated sleeve within an intended body part. A fluid input is structured for removable connection to a fluid source and is disposed on the sleeve, in fluid communication with the bladder. An access opening is formed on the proximal portion and is cooperatively dimensioned with the hollow interior to removably receive any one of a plurality of different types of positioning instruments within the sleeve.

19 Claims, 11 Drawing Sheets

Related U.S. Application Data continuation-in-part of application No. 14/599,817, filed on Jan. 19, 2015, now abandoned.

(58) Field of Classification Search
CPC ........ A61B 17/12022; A61B 17/12027; A61B 17/12131; A61B 2017/22051; A61B 2017/1205; A61B 2017/12054; A61B 2017/242; A61B 2017/246; A61M 29/02; A61M 1/00; A61M 1/0064
See application file for complete search history.

(56) References Cited

U.S. PATENT DOCUMENTS

| | | |
|---|---|---|
| 3,799,170 A | 3/1974 | Walsh et al. |
| 3,903,893 A | 9/1975 | Scheer |
| 4,311,146 A | 1/1982 | Wonder |
| 4,312,353 A | 1/1982 | Shahbabian |
| 4,341,218 A | 7/1982 | U |
| 4,819,637 A | 4/1989 | Dormandy, Jr. et al. |
| 5,021,043 A | 6/1991 | Becker et al. |
| 5,035,686 A | 7/1991 | Crittenden et al. |
| 5,098,379 A | 3/1992 | Conway et al. |
| 5,169,386 A | 12/1992 | Becker et al. |
| 5,171,297 A | 12/1992 | Barlow et al. |
| 5,176,638 A | 1/1993 | Don Michael |
| 5,304,123 A | 4/1994 | Atala et al. |
| 5,370,899 A | 12/1994 | Conway et al. |
| 5,395,331 A * | 3/1995 | O'Neill ............. A61M 25/0023 604/103.08 |
| 5,569,219 A | 10/1996 | Hakki et al. |
| 5,681,344 A | 10/1997 | Kelly |
| 5,788,681 A | 8/1998 | Weaver et al. |
| 6,325,777 B1 | 12/2001 | Zadno-Azizi et al. |
| 6,447,540 B1 | 9/2002 | Fontaine et al. |
| 7,108,706 B2 | 9/2006 | Hogle |
| 7,169,163 B2 | 1/2007 | Becker |
| 7,462,175 B2 | 12/2008 | Chang et al. |
| 7,500,971 B2 | 3/2009 | Chang et al. |
| 7,559,925 B2 | 7/2009 | Goldfarb et al. |
| 7,578,099 B2 | 8/2009 | Schlegel |
| 7,591,832 B2 | 9/2009 | Eversull et al. |
| 7,604,627 B2 | 10/2009 | Kojouri |
| 7,645,272 B2 | 1/2010 | Chang et al. |
| 7,654,997 B2 | 2/2010 | Makower et al. |
| 7,670,284 B2 | 3/2010 | Padget et al. |
| 7,678,099 B2 | 3/2010 | Ressemann et al. |
| 7,695,490 B2 | 4/2010 | Hogle |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,740,642 B2 | 6/2010 | Becker |
| 7,744,620 B2 | 6/2010 | Pedersen et al. |
| 7,753,929 B2 | 7/2010 | Becker |
| 7,753,930 B2 | 7/2010 | Becker |
| 7,771,409 B2 | 8/2010 | Chang et al. |
| 7,785,315 B1 | 8/2010 | Muni et al. |
| 7,799,048 B2 | 9/2010 | Hudson et al. |
| 7,803,150 B2 | 9/2010 | Chang et al. |
| 7,854,744 B2 | 12/2010 | Becker |
| 7,879,061 B2 | 2/2011 | Keith et al. |
| 7,918,871 B2 | 4/2011 | Truitt et al. |
| D643,115 S | 8/2011 | Gonzales et al. |
| 8,080,000 B2 | 12/2011 | Makower et al. |
| 8,088,101 B2 | 1/2012 | Chang et al. |
| 8,090,433 B2 | 1/2012 | Makower et al. |
| 8,100,933 B2 | 1/2012 | Becker |
| 8,114,113 B2 | 2/2012 | Becker |
| 8,137,375 B2 | 3/2012 | Hudson et al. |
| 8,142,422 B2 | 3/2012 | Makower et al. |
| 8,146,400 B2 | 4/2012 | Goldbar et al. |
| 8,172,828 B2 | 5/2012 | Chang et al. |
| 8,277,478 B2 | 10/2012 | Drontle et al. |
| 8,282,667 B2 | 10/2012 | Drontle et al. |
| 8,317,816 B2 | 11/2012 | Becker |
| 8,394,400 B2 | 3/2013 | Bourne et al. |
| D679,803 S | 4/2013 | Carter |
| 8,414,473 B2 | 4/2013 | Jenkins et al. |
| 8,425,457 B2 | 4/2013 | John et al. |
| 8,506,589 B2 | 8/2013 | Maloney |
| 8,529,546 B2 | 9/2013 | Alvarez |
| 8,568,438 B2 | 10/2013 | Burbank et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,657,846 B2 | 2/2014 | Keith et al. |
| 8,715,169 B2 | 5/2014 | Chang et al. |
| 8,721,591 B2 | 5/2014 | Chang et al. |
| 8,740,844 B2 | 6/2014 | Freyman et al. |
| 8,747,389 B2 | 6/2014 | Goldfarb et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,764,786 B2 | 7/2014 | Becker |
| 8,777,926 B2 | 7/2014 | Chang et al. |
| 8,833,373 B2 | 9/2014 | Barodka |
| 8,834,513 B2 | 9/2014 | Hanson et al. |
| 8,858,586 B2 | 10/2014 | Chang et al. |
| 8,864,746 B2 | 10/2014 | Becker |
| 8,888,686 B2 | 11/2014 | Drontle et al. |
| 8,894,614 B2 | 11/2014 | Muni et al. |
| 8,905,922 B2 | 12/2014 | Makower et al. |
| 8,915,938 B2 | 12/2014 | Keith et al. |
| 8,936,612 B2 | 1/2015 | Suehara |
| 8,951,225 B2 | 2/2015 | Evard et al. |
| 8,968,269 B2 | 3/2015 | Becker |
| 9,011,412 B2 | 4/2015 | Albritton, IV et al. |
| 9,050,440 B2 | 6/2015 | Becker |
| 9,089,258 B2 | 7/2015 | Goldfarb et al. |
| 9,095,646 B2 | 8/2015 | Chow et al. |
| 9,101,384 B2 | 8/2015 | Makower et al. |
| 9,101,430 B2 | 8/2015 | Müller et al. |
| 9,101,739 B2 | 8/2015 | Lesch, Jr. et al. |
| 9,107,687 B2 | 8/2015 | Kinoshita et al. |
| 9,167,961 B2 | 10/2015 | Makower et al. |
| 9,192,748 B2 | 11/2015 | Ressemann et al. |
| 9,199,058 B2 | 12/2015 | Lentz |
| 9,204,893 B2 | 12/2015 | Rizk et al. |
| 9,220,879 B2 | 12/2015 | Chang et al. |
| 9,226,800 B2 | 1/2016 | Burg et al. |
| 9,248,266 B2 | 2/2016 | Chandler et al. |
| 9,282,986 B2 | 3/2016 | Hanson et al. |
| 9,339,637 B2 | 5/2016 | Drontle et al. |
| 9,370,649 B2 | 6/2016 | Chang et al. |
| 9,370,650 B2 | 6/2016 | Hanson et al. |
| 9,399,121 B2 | 7/2016 | Goldfarb et al. |
| 9,457,175 B2 | 10/2016 | Becker |
| 9,463,307 B2 | 10/2016 | Vaccaro et al. |
| 9,486,614 B2 | 11/2016 | Drontle et al. |
| 9,498,239 B2 | 11/2016 | Schreck et al. |
| 9,510,743 B2 | 12/2016 | Chandler et al. |
| 9,550,049 B2 | 1/2017 | Hanson et al. |
| 9,554,691 B2 | 1/2017 | Goldfarb et al. |
| 9,554,817 B2 | 1/2017 | Goldfarb et al. |
| 9,572,954 B2 | 2/2017 | Pinchuk et al. |
| 9,579,448 B2 | 2/2017 | Chow et al. |
| 9,603,506 B2 | 3/2017 | Goldfarb et al. |
| 9,610,428 B2 | 4/2017 | Muni et al. |
| 9,649,477 B2 | 5/2017 | Muni et al. |
| 9,687,263 B2 | 6/2017 | Schreck et al. |
| 9,694,163 B2 | 7/2017 | Chandler et al. |
| 9,700,326 B2 | 7/2017 | Morriss et al. |
| 9,700,705 B2 | 7/2017 | Lesch, Jr. et al. |
| 9,700,706 B2 | 7/2017 | Becker |
| 9,713,700 B2 | 7/2017 | Chang et al. |
| 9,757,018 B2 | 9/2017 | Kesten et al. |
| 9,770,577 B2 | 9/2017 | Li et al. |
| 9,775,975 B2 | 10/2017 | Ressemann et al. |
| 9,820,688 B2 | 11/2017 | Jenkins et al. |
| 9,827,367 B2 | 11/2017 | Perry et al. |
| 9,833,130 B2 | 12/2017 | Schaeffer et al. |
| 9,839,347 B2 | 12/2017 | Chandler et al. |
| 9,931,026 B2 | 4/2018 | Ha et al. |

(56) References Cited

U.S. PATENT DOCUMENTS

| | | |
|---|---|---|
| 9,955,852 B2 | 5/2018 | Kesten et al. |
| 9,987,025 B2 | 6/2018 | Becker |
| 9,999,752 B2 | 6/2018 | Becker |
| 10,004,863 B2 | 6/2018 | Vazales et al. |
| 10,016,580 B2 | 7/2018 | Chandler et al. |
| 10,022,525 B2 | 7/2018 | Hanson et al. |
| 10,034,682 B2 | 7/2018 | Muni et al. |
| 10,065,028 B2 | 9/2018 | Liberatore et al. |
| 10,085,889 B2 | 10/2018 | Chan et al. |
| 10,098,652 B2 | 10/2018 | Goldfarb et al. |
| 10,124,154 B2 | 11/2018 | Evard et al. |
| 10,137,285 B2 | 11/2018 | Jenkins et al. |
| 10,143,591 B2 | 12/2018 | Ha et al. |
| 10,154,850 B2 | 12/2018 | Janjua |
| 10,166,369 B2 | 1/2019 | Jenkins et al. |
| 10,179,002 B2 | 1/2019 | Wasicek et al. |
| 10,179,227 B2 | 1/2019 | Lam et al. |
| 10,183,153 B2 | 1/2019 | Kesten et al. |
| 10,188,413 B1 | 1/2019 | Morriss et al. |
| 10,206,821 B2 | 2/2019 | Campbell et al. |
| 10,238,845 B2 | 3/2019 | Ha et al. |
| 10,244,935 B2 | 4/2019 | Ha et al. |
| 10,271,719 B2 | 4/2019 | Morriss et al. |
| 10,271,871 B2 | 4/2019 | Palushi et al. |
| 10,300,257 B2 | 5/2019 | Wu et al. |
| 10,307,519 B2 | 6/2019 | Drontle et al. |
| 10,335,319 B2 | 7/2019 | Wasicek et al. |
| 10,350,396 B2 | 7/2019 | Chan et al. |
| 10,362,965 B2 | 7/2019 | Kesten et al. |
| 10,363,402 B2 | 7/2019 | Drontle et al. |
| 10,376,416 B2 | 8/2019 | Clifford et al. |
| 10,383,992 B2 | 8/2019 | Goldfarb et al. |
| 10,426,925 B2 | 10/2019 | Schaeffer |
| 10,441,758 B2 | 10/2019 | Muni et al. |
| 10,456,519 B2 | 10/2019 | Ngo-Chu |
| 10,463,242 B2 | 11/2019 | Kesten et al. |
| 10,485,609 B2 | 11/2019 | Palushi et al. |
| 10,492,810 B2 | 12/2019 | Chang et al. |
| 10,493,251 B2 | 12/2019 | Ha et al. |
| 10,500,380 B2 | 12/2019 | Chang et al. |
| 10,507,310 B2 | 12/2019 | Matlock et al. |
| 10,512,763 B2 | 12/2019 | Jenkins et al. |
| 10,512,764 B2 | 12/2019 | Ngo-Chu et al. |
| 10,517,608 B2 | 12/2019 | Jenkins et al. |
| 10,524,814 B2 | 1/2020 | Chang et al. |
| 10,524,869 B2 | 1/2020 | Jenkins et al. |
| 10,549,076 B2 | 2/2020 | Kesten et al. |
| 10,561,829 B2 | 2/2020 | Hanson et al. |
| 10,569,060 B2 | 2/2020 | Jenkins et al. |
| 10,589,072 B2 | 3/2020 | Chandler et al. |
| 10,602,966 B2 | 3/2020 | Makower |
| 10,603,472 B2 | 3/2020 | Gliner et al. |
| 10,610,308 B2 | 4/2020 | Sema et al. |
| 10,625,062 B2 | 4/2020 | Matlock et al. |
| 10,631,756 B2 | 4/2020 | Kim et al. |
| 10,631,890 B2 | 4/2020 | Palushi et al. |
| 10,639,457 B2 | 5/2020 | Becker |
| 10,639,462 B2 | 5/2020 | Matlock et al. |
| 10,646,701 B2 | 5/2020 | Ressemann et al. |
| 10,682,503 B2 | 6/2020 | Gerrans et al. |
| 10,687,690 B2 | 6/2020 | Kesten et al. |
| 10,695,080 B2 | 6/2020 | Chang et al. |
| 10,695,537 B2 | 6/2020 | Muni et al. |
| 10,702,295 B2 | 7/2020 | Jenkins et al. |
| 10,709,880 B2 | 7/2020 | Johnson et al. |
| 10,716,629 B2 | 7/2020 | Goldfarb et al. |
| 10,716,709 B2 | 7/2020 | Morriss et al. |
| 10,722,109 B2 | 7/2020 | Kermani |
| 10,736,647 B2 | 8/2020 | Palushi et al. |
| 10,736,784 B2 | 8/2020 | Ngo-Chu et al. |
| 10,772,489 B2 | 9/2020 | Govari et al. |
| 10,779,752 B2 | 9/2020 | Kim et al. |
| 10,779,891 B2 | 9/2020 | Clopp |
| 10,786,311 B2 | 9/2020 | Salazar et al. |
| 10,806,477 B2 | 10/2020 | Goldfarb et al. |
| 10,806,849 B2 | 10/2020 | Newhauser, Jr. et al. |
| 10,813,547 B2 | 10/2020 | Makower et al. |
| 10,835,327 B2 | 11/2020 | Palushi et al. |
| 10,835,723 B2 | 11/2020 | Hanson et al. |
| 10,842,978 B2 | 11/2020 | Evard et al. |
| 10,856,727 B2 | 12/2020 | Goldfarb et al. |
| 10,857,333 B2 | 12/2020 | Ngo-Chu et al. |
| 10,864,046 B2 | 12/2020 | Salazar et al. |
| 10,874,838 B2 | 12/2020 | Goldfarb et al. |
| 10,874,839 B2 | 12/2020 | Matlock et al. |
| 10,898,693 B2 | 1/2021 | Gerrans et al. |
| 10,905,820 B2 | 2/2021 | Chow et al. |
| 2004/0127850 A1 | 7/2004 | Steadham et al. |
| 2004/0131808 A1 | 7/2004 | Schoenle et al. |
| 2004/0254528 A1* | 12/2004 | Adams ............... A61M 25/00 604/96.01 |
| 2005/0113859 A1 | 5/2005 | Elliott et al. |
| 2006/0063973 A1 | 3/2006 | Makower et al. |
| 2008/0091067 A1 | 4/2008 | Dollar |
| 2008/0172038 A1 | 7/2008 | Dollar et al. |
| 2009/0076439 A1 | 3/2009 | Dollar et al. |
| 2009/0076446 A1 | 3/2009 | Dubuclet, IV et al. |
| 2009/0088728 A1 | 4/2009 | Dollar et al. |
| 2009/0198216 A1 | 8/2009 | Muni et al. |
| 2010/0087709 A1 | 4/2010 | Bertolero et al. |
| 2010/0234724 A1 | 9/2010 | Jacobsen et al. |
| 2011/0112512 A1 | 5/2011 | Muni et al. |
| 2011/0152788 A1 | 6/2011 | Hotter |
| 2011/0270081 A1 | 11/2011 | Burg et al. |
| 2012/0053404 A1 | 3/2012 | Schreck et al. |
| 2013/0041463 A1 | 2/2013 | Ressemann |
| 2013/0066358 A1 | 3/2013 | Nalluri et al. |
| 2013/0253632 A1 | 9/2013 | Schreck |
| 2013/0261550 A1 | 10/2013 | Edgren et al. |
| 2014/0031852 A1 | 1/2014 | Edgren et al. |
| 2014/0031853 A1 | 1/2014 | Suehara |
| 2014/0107427 A1 | 4/2014 | Chow et al. |
| 2014/0213968 A1 | 7/2014 | Vaccaro et al. |
| 2014/0277058 A1 | 9/2014 | Wu |
| 2016/0270863 A1 | 9/2016 | Makower |
| 2016/0287059 A1 | 10/2016 | Ha et al. |
| 2016/0310041 A1 | 10/2016 | Jenkins et al. |
| 2018/0110407 A1 | 4/2018 | Makower et al. |

FOREIGN PATENT DOCUMENTS

| | | |
|---|---|---|
| WO | WO 2018/146694 | 8/2018 |
| WO | WO 2019/034932 | 2/2019 |
| WO | WO 2019/123319 | 6/2019 |
| WO | WO 2019/209682 | 10/2019 |
| WO | WO 2019/234537 | 12/2019 |
| WO | WO 2020/221882 | 11/2020 |
| WO | WO 2020/221885 | 11/2020 |
| WO | WO 2021/038484 | 3/2021 |

OTHER PUBLICATIONS

Gottmann, et al., Successful Treatment of Recurrent Post-Operative Frontal Sinus Stenoses by Balloon Dilatation, CIRSE Abstract and Presentation (Oct. 5, 2002).

Gutman, et al., The Use of the Foley Catheter in the Treatment of Zygomatic Bone Fractures, Brit. J. oral Surg., vol. 2, pp. 153-157 (1964).

Jackson, et al., Balloon Technic for Treatment of Fractures of the Zygomatic Bone, J. oral Surg., vol. 14, pp. 14-19 (Jan. 1956).

Lanza, M.D., Donald C., "Postoperative Care and Avoiding Frontal Recess Stenosis", The International Advanced Sinus Symposium, Phila., PA, Jul. 1993 (2 page).

Podoshin, et al., Balloon Techniques for Treatment of Frontal Sinus Fractures, Journal of Laryngology and Otology, vol. 81, pp. 1157-1161 (Oct. 1967).

International Search Report and Written Opinion for International Application No. PCT/US2020/035738, Notification dated Aug. 31, 2020.

\* cited by examiner

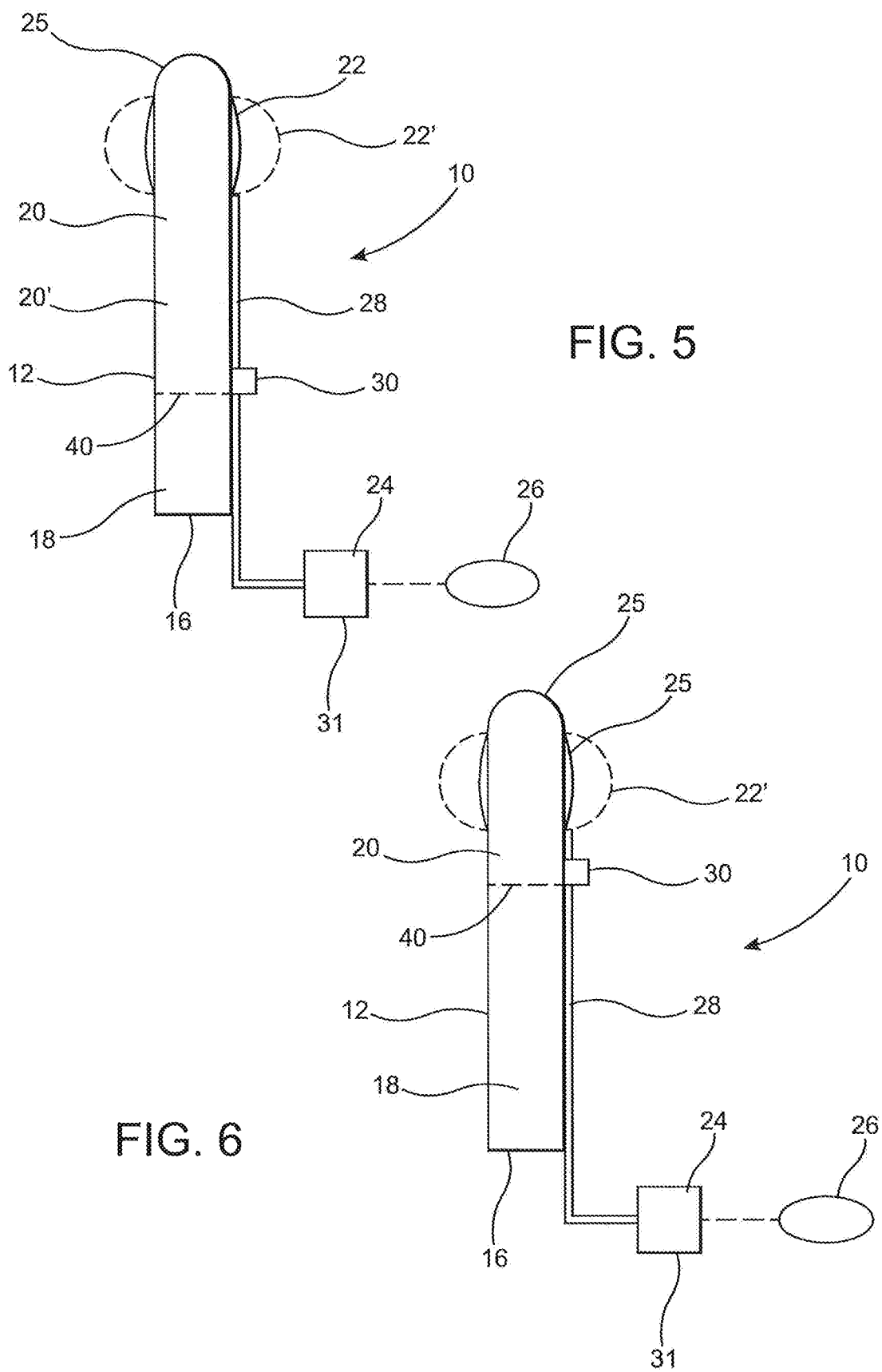

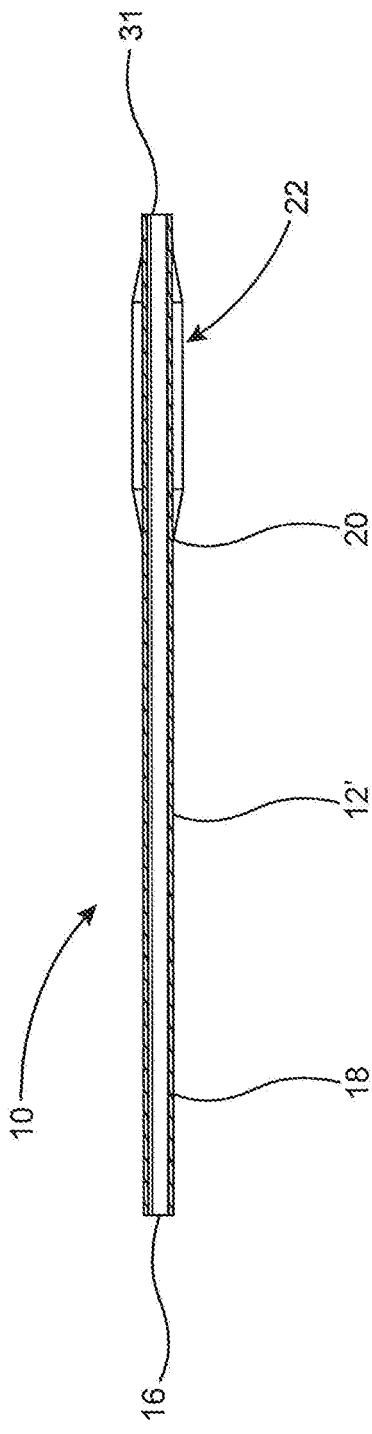
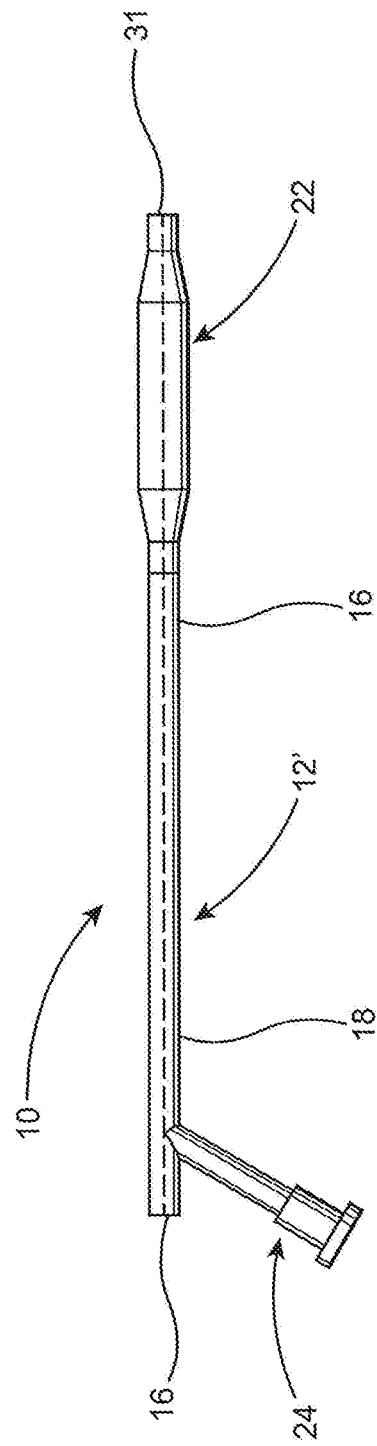

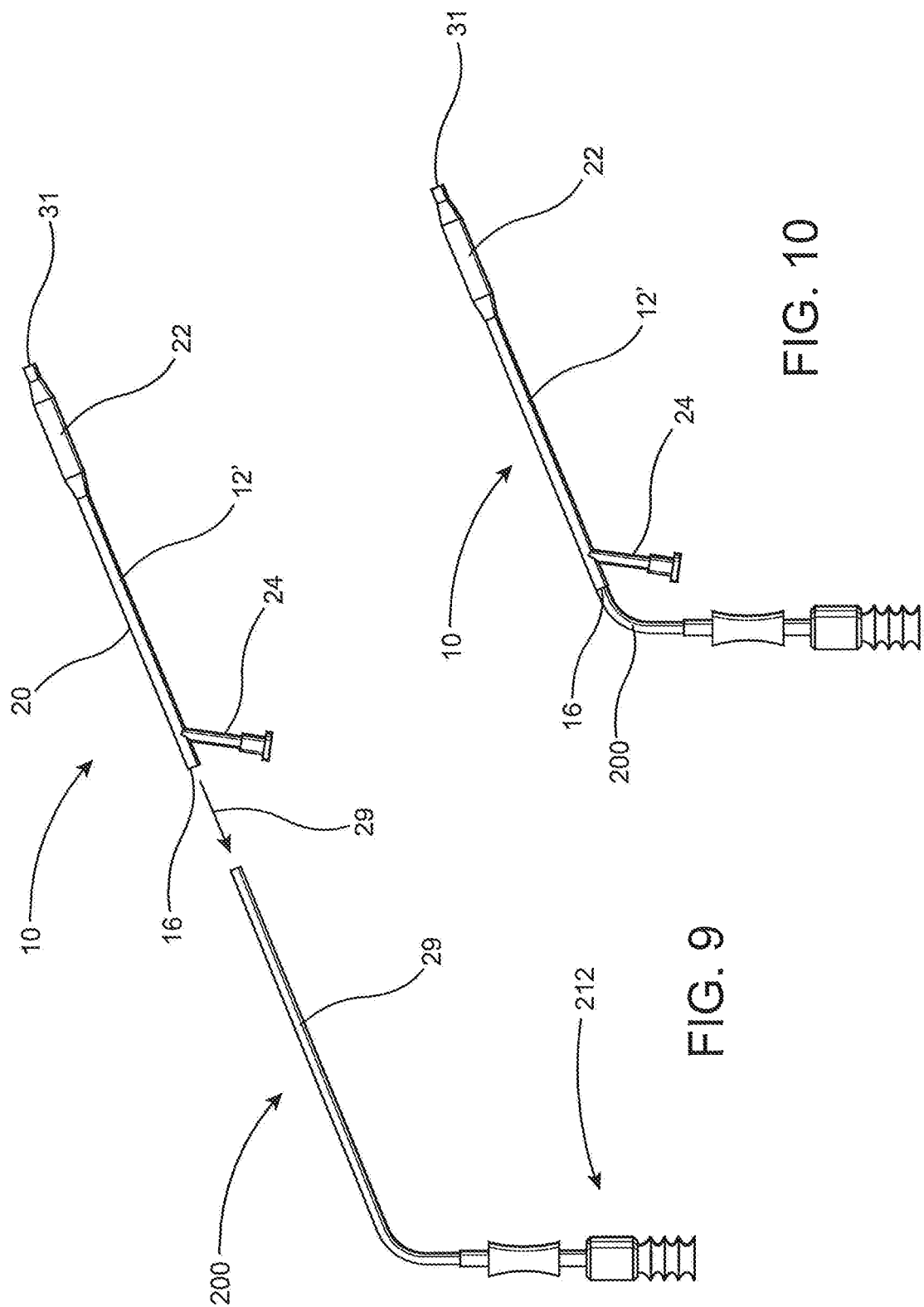

DILATOR DEVICE

CROSS-REFERENCE TO RELATED APPLICATIONS

This application is a continuation of U.S. patent application Ser. No. 15/635,666, filed Jun. 28, 2017, which is a continuation-in-part of U.S. patent application Ser. No. 14/599,817, filed Jan. 19, 2015, each of which are hereby incorporated by reference herein in their entireties. Any and all applications, if any, for which a foreign or domestic priority claim is identified in the Application Data Sheet of the present application are hereby incorporated by reference under 37 CFR 1.57.

BACKGROUND

Field of the Invention

This invention is directed to a dilator device comprising a flexible material, hollow sleeve or sheath having an expandable bladder on a proximal portion thereof. The sleeve and bladder is structured to be disposed in an operative position relative to a dilation site by inserting any one of a plurality of different positioning instruments within the hollow interior.

Description of the Related Art

Paranasal sinuses of the human body comprise a plurality of right and left sinus cavities including frontal, ethmoid, sphenoid and maxillary sinus cavities. The maxillary sinuses are the largest and most common site for sinus infection. In addition, the paranasal sinuses are lined with mucus-producing tissue that is in communicating relation with the nasal cavity. Mucus produced by the indicated tissue slowly drains out of each sinus through an opening or ostium. If the mucus draining tissue of a corresponding passageway becomes inflamed, the corresponding cavities through the passageways can become blocked. Such blockage interferes with the drainage of mucous typically resulting in occlusion of the sinus ostium and mucosal congestion within the paranasal sinuses. Chronic congestion, of this type, within the sinuses can cause damage to the tissue that lines the sinus and a resulting sinus infection.

The term "sinusitis" refers generally to any inflammation or infection of the paranasal sinuses caused by bacteria, viruses, mold, allergies or combination of such factors. In more practical terms, it is estimated that chronic sinusitis results in millions of individuals visiting physician's offices on a yearly basis in the United States. Further, individuals suffering from sinusitis typically experience at least some symptoms including, but not limited to, headaches, facial pain, nasal congestion, difficulty in breathing and pain in the oral cavity. In situations where maxillary sinusitis cannot be successfully treated with antibiotics, decongestants and steroid nasal sprays, other procedures including catheter-based interventions are sometimes utilized. Accordingly, relief from such symptoms and causal factors includes restoring blocked mucus flow. As set forth above, various methods and devices for treatment of sinusitis and other conditions involving blocked mucus are known and include the dilating of the sinus ostia with various types of dilator devices. Typically, such devices are inserted trans-nasally or by a trans-canine fossa approach.

In various medical procedures including, but not limited to, the dilation of the paranasal sinus areas dilation devices, including balloon catheters, have been used. Expandable catheters have been available for many years. However, in recent years additional development has been directed to the utilization, application and design of detachable catheters capable of being used in various medical procedures. In use, the catheter or other positioning instrument may be integrally associated with the expandable or inflatable devices designed and structured to be passed along a sometimes circuitous path to reach the site intended to be dilated.

However, one problem associated with conventional and/or known devices of this type include the reliable maintenance of the dilator device in an inflated or expanded condition after it is in position. Moreover, the inflator device must be reliably sealed while allowing it to be detached from the positioning instrument. Further, it is frequently desired to maintain and intended operative position of the dilator device for a relatively extended time without damaging it or the surrounding tissue. It is recognized that while known instrumentation of this type may be at least minimally successful for accomplishing the intended result, challenges relating to the design, manufacture and use of a simplified, inexpensive, more effective and efficient dilator device.

Attempts to solve problems and disadvantages of the type set forth above have sometimes resulted in the use of a double lumen catheter instrument operable to detach the balloon or inflated portion from the catheter. As such, the inner catheter may be manipulated into position relative to the dilation site and the balloon or expandable portion is inflated. The outer catheter is then positioned against the base of the expansion portion and the inner catheter is pulled backwards resulting in a separation of the balloon or expansion portion from the inner catheter. At the same time included threads are disposed at the base of the expansion portion in order to maintain it in an inflated or expanded orientation. As should be apparent, instrumentation associated with a double catheter approach may be considered overly complex.

Other disadvantages with known inflation devices include the use of balloons or like expandable structures being used with only a specific positioning instrument, wherein the balloon or expandable structure may be integrated or connected directly to the specialized positioning instrument. This obviously involves the necessity of selecting different appropriate positioning instruments for each of a possible plurality of procedures or dilation sites being treated.

Accordingly, there is a need in this area for an improved dilator device which may be operatively positioned relative to an intended dilation site in a simple and efficient manner without requiring the use of specialized, integrated instrumentation. More specifically, such an improved and proposed dilating device would have the advantage of being usable with any one of a plurality of different positioning instruments. As a result the same dilator device can be used with an appropriate positioning instrument which is structured to best position the dilator device in an operative position relative to the intended dilation site.

SUMMARY

The present invention is directed to a dilator device operative to dilate or expand any of a plurality of different regions, locations, areas, etc. in the human body such as, but not limited to, the paranasal sinuses.

In more specific terms, the dilator device of the present invention comprises an elongated sleeve formed of a flexible material which includes a distal portion and a proximal portion. Moreover, the sleeve includes a hollow interior extending along at least a majority and/or the entirety of the length of the sleeve and along both the proximal and distal portions. An access opening or like structure is formed preferably on the proximal portion such as, but not limited to, the end or extremity of the proximal portion in communicating relation with a hollow interior.

In addition, a bladder is formed on or connected to the distal portion preferably at or adjacent to the distal end or extremity. Further, the bladder is capable of being inflated or otherwise expanded into an inflated or expanded orientation. When so oriented, the bladder extends radially outward from an exterior of the distal portion of the sleeve. In at least one preferred embodiment, a preferred expanded or inflated orientation of the bladder includes it transversely surrounding the sleeve, such as by extending along a transverse circumference thereof. It is emphasized that the size, configuration and disposition of the bladder, when in its expanded or inflated orientation may vary dependent, at least in part, on the area, location, or site of the body portion, to be dilated.

The versatility of the dilator device of the present invention is significantly enhanced by structuring it to be used in combination with any one of a plurality of different positioning instruments. As set forth above, known or conventional dilator assemblies, including those used in the medical profession, are frequently defined by both the positioning instrument and an expandable or a dilating structure assembled or designed as operatively and/or structurally integrated parts. As a result, many of the conventional dilator assemblies are not adaptable for the dilation of specific body parts. To the contrary, devices and assemblies of this type may be specifically structured or designed for use on a specific area or location of the body.

Accordingly, one or more preferred embodiments of the present invention include the aforementioned sleeve being dimensioned, configured and structured to be disposed in a sheath-like manner on or over any one of a plurality of different positioning instruments. As a result, the dilator sleeve can be used to dilate different areas or parts of the human body by being disposed in a preferred operative position relative to the dilation site by using an appropriately dimensioned, configured and/or structured positioning instrument intended to reach or approach the dilation site. Moreover, the adaptation of the dilator sleeve to different positioning instruments is facilitated by the forming of the sleeve from a material having sufficient flexibility to substantially adapt or conform to at least a portion of the positioning instrument disposed or received within the hollow interior of the sleeve. To those familiar with dilation instrumentation, it should be recognized that the positioning instrument may be flexible, semi-rigid, substantially or at least partially rigid or otherwise appropriately structured to reach an intended dilation site. Also, the selected positioning instrument should be structured to efficiently dispose the bladder of the dilator sleeve in and appropriate, operative position to accomplish the intended dilation.

Additional structural and operative features of one or more preferred embodiments of the dilator device include the provision of a fluid input connected to the sleeve in fluid communication with the bladder. Further, the fluid input is structured for removable connection to a fluid source, which may be independent of the positioning instrument. Dependent, at least in part, on the structural and operative features of the bladder, the fluid source may be a source of gas used to expand the bladder by "inflation" or a source of liquid or other appropriate fluid used to expand the bladder. As used herein, the terms "inflate" or its equivalent may be used interchangeably with the term "expand" or its equivalent, regardless of the fluid being delivered to the interior of the bladder which cause its outward, radial extension or position. In addition, the fluid input also includes or is used in cooperation with a flow restrictor such as, but not limited to, a one-way check valve. The provision and disposition of the flow restrictor allows fluid flow from the fluid source into and through the fluid input to and into the bladder so as to facilitate its inflation and/or expansion. In addition, the flow restrictor is structured to restrict fluid flow in an opposite direction, from the bladder to an exterior of the sleeve, or other location in order to maintain the bladder in the inflated or expanded orientation. However, the flow restrictor is further structured and operative to allow a deflation or collapse of the bladder such as, but not limited to, the removal of the bladder and/or dilator device from an operative orientation relative to the area being dilated. As set forth in greater detail hereinafter, the fluid input as well as the flow restrictor may be disposed at various locations on the sleeve dependent upon the additional operative features, intended use and cooperative structuring of the sleeve.

Accordingly, one or more preferred embodiments of the dilator device may include additional structural and operative features incorporated within the dilator sleeve. More specifically, the sleeve may include a frangible portion or separable portion disposed in interconnecting relation between the distal portion and a proximal portion. The frangible or separable portion of the sleeve may include a variety of different structural configurations such as, but not limited to, a weakened seam or weakened segment line extending circumferentially or otherwise disposed in interconnecting relation between the proximal and distal portions. The frangible or separable portion is structured to facilitate a separation of the distal and proximal portions from one another when a predetermined pulling or other directed force is exerted on the proximal portion. The use of the separable embodiment(s) may be applicable in situations where it is intended or preferred to maintain the distal portion and inflated or expanded bladder in the operative position relative to the dilation site for an extended period.

Further by way of example, when the separable embodiment(s) of the sleeve is intended to dilate a portion of the nasal passage or sinus area, the bladder may be disposed in the aforementioned operative position relative to the dilation site. After expansion or inflation of the bladder, the proximal portion is cooperatively dimensioned with a remainder of the sleeve so as to be accessible for purposes of exerting the aforementioned pulling or other directed force thereon. As indicated, the exertion of such a force will cause a separation of the proximal portion from the distal portion, while leaving the expanded bladder I the operative position relative to the dilation site. Further, one or more separable embodiments of the dilator sleeve may also include a tail portion connected to the distal portion. The tail portion is further dimensioned so as to be accessible by medical personnel, possibly using appropriate instrumentation, for eventual removal of the remainder of the proximal portion and bladder, after the proximal portion has been separated or removed.

Additional features of the one or more separable embodiments of the dilator sleeve may include the aforementioned fluid input and/or flow restrictor being disposed on the distal portion or other appropriate portion of the sleeve so as to remain in communicating relation with the inflated or expanded bladder. This will assure that the bladder will continuously remain in the expanded or inflated orientation subsequent to the removal of the proximal portion, during an extended period of dilation.

In preferred embodiments according to the present invention, the elongated sleeve comprises a predetermined structural integrity that facilitates positioning the dilator device within the paranasal sinuses. The predetermined structural integrity may be at least partially defined by the elongated sleeve comprising a preferred rigidity. The preferred rigidity comprises the sleeve being sufficiently rigid to move or penetrate within the paranasal sinuses while also being sufficiently flexible to conform to the positioning instruments or to the geometry of the paranasal sinuses. The preferred rigidity may be at least partially defined by the wall thickness and the materials of the elongated sleeve. The elongated sleeve may comprise an inner layer and an outer layer. The conduit that transports the fluid that inflates the balloon may be disposed between both layers. Alternatively, the elongated sleeve may comprise a single outer layer wherein the conduit disposed substantially within the outer layer.

Further features of the dilator device of the present invention comprise a sleeve having a tip with a predetermined configuration. The predetermined configuration may be a substantially tapered configuration of the tip that facilitates positioning the sleeve within the paranasal sinuses. More specifically, the tapered configuration of the tip facilitates entry of the sleeve into smaller openings. The tip should comprise an open end of smaller size than that of the positioning instrument so that the positioning instrument does not pass there through. Instead, further movement of the positioning instrument should result in a substantially corresponding movement of the elongated sleeve.

The dilator device 10 of the present invention may be used in conjunction with a suction component that can exert negative pressure to an intended location. The hollow interior should be dimensioned and configured to receive therein a suction component and to permit reciprocal movement of the same within the hollow interior. Likewise, the sleeve should also be able to reciprocally move relative to the suction component. The open end should be of sufficient size so that the suction component may pass there through to reach an otherwise deeper intended location within the paranasal sinuses.

Additional features of the present invention include a navigation interface. The navigation interface may be at least partially defined as an external device that may be located on the exterior of the body. For example, the external device may be located on the face of a person, and in substantial alignment with the paranasal sinuses. The external device may be configured to substantially duplicate the movement of the dilator device by forming an at least partially operable magnetic interface with the tip of the sleeve. Accordingly, the external device may comprise a magnet while the tip may comprise a material capable of being attracted to the magnet. The magnetic interface may be used to determine or track an at least approximate position of the dilator device within the paranasal sinuses. The navigation interface may also be at least partially defined as a component observable on a variety of imaging capabilities. The tip may comprise a material that may act as a contrast agent on the particular imaging capability. For example, the tip may comprise barium sulfate which is a contrast agent that is viewable on an x-ray.

Yet additional features of the present invention include the dilator device comprising an irrigation structure configured to provide irrigation to an intended body part. The tip may comprise an irrigation portion having at least one opening disposed in fluid communication with at least a portion of the hollow interior and configured to provide irrigation. Consequently, a fluid may pass through the hollow interior and exit through the irrigation opening(s) to irrigate the intended body part.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 5 is a schematic representation of yet another preferred embodiment of the dilator device of the present invention.

FIG. 6 is a schematic representation of yet another preferred embodiment of the dilator device of the present invention.

FIG. 8A is a schematic representation in cross-section of yet another preferred embodiment of the dilator device of the present invention.

FIG. 8B is a schematic representation of an exterior view of the embodiment of the dilator device as represented in FIG. 8A.

FIG. 9 is a schematic representation in exploded form of the embodiment of the dilator device as represented in FIG. 8 in a position to be mounted on a selected positioning instrument.

FIG. 10 is a schematic representation of the embodiment of the dilator device of FIGS. 8 and 9 mounted in an operative position on a selected positioning instrument, as also represented in FIG. 9.

Like reference numerals refer to like parts throughout the several views of the drawings.

DETAILED DESCRIPTION OF THE PREFERRED EMBODIMENT

Figure 1:
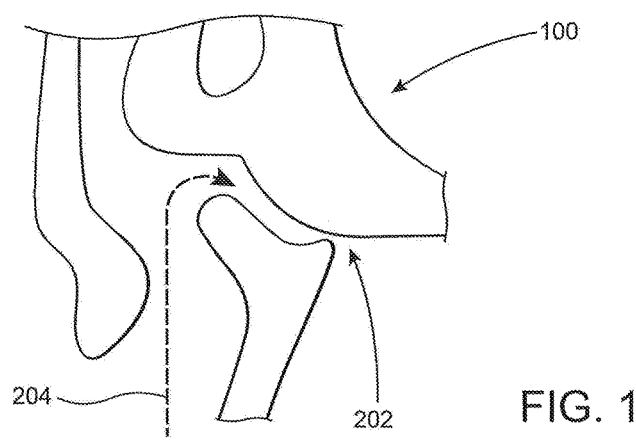
FIG. 1 is a schematic representation of a paranasal sinus area of the human body and possible dilation site.
Figure 2:
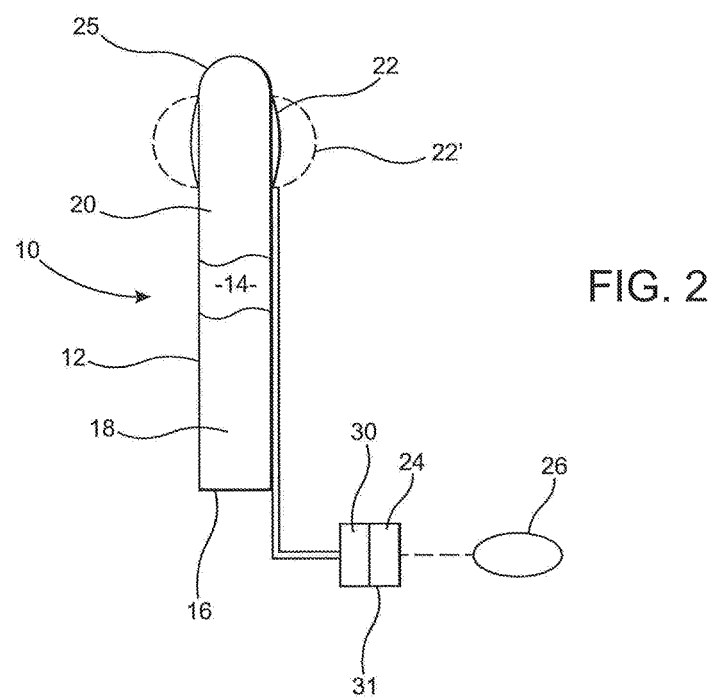
FIG. 2 is a schematic representation of a debt dilator device of the present invention, in a non-expanded orientation, mounted on any one of it possible plurality of positioning instruments.

As represented in FIGS. 1-10, the present invention is directed to a dilator device generally indicated as 10. As explained in greater detail hereinafter, the dilator device 10 may be used to dilate various parts of the body including, but not limited to, the paranasal sinuses 100 as schematically represented in FIG. 1.

Accordingly, the dilator device 10 includes an elongated sleeve or sheath 12 formed of a conformable, sufficiently flexible material to substantially and/or at least partially conform to and be positioned by any one of a plurality of different positioning instruments, generally indicated as 200. Further, the sleeve or sheath 12 includes a hollow interior 14 extending along at least a majority or the entirety of its length. The sleeve 12 also includes an access opening 16 preferably, but not necessarily, disposed at an end or extremity of a proximal portion 18. The sleeve 12 also includes what may be accurately described as a distal portion 20 at least partially defining the opposite end and extremity of the sleeve or sheath 12. It is also to be noted that in the embodiment of the sheath or sleeve 12, as represented in FIGS. 2-6, the outer extremity of the distal portion 20 includes a closed end 25.

Therefore, the dimensions of the access opening 16 and the hollow interior 14 as well as the overall length of the sleeve or sheath 12 allows any one of a plurality of positioning instruments to be disposed within the interior 14 and extend along at least a majority of the length thereof. Further, the aforementioned flexible material from which the sleeve or sheath 12 is formed facilitates an at least partial conformance of the sleeve 12 to the exterior of the positioning instrument 200 or more specifically to a portion of the positioning instrument 200 disposed within the interior 14 and extending along the length of the sleeve 12. Such conformance of the sleeve 12 to the selected positioning instrument facilitates the movement and accurate positioning of the sleeve, in an operative orientation, as the positioning instrument and sleeve move through the paranasal sinus area or other area to be dilated. From a review of the paranasal sinuses 100, as represented in FIG. 1, it is apparent that proper positioning of the sleeve 12 in the operative orientation or position relative to a dilation site such as, but not limited to, the maxillary ostium 202, may involve passage of the sleeve 12 and the positioning instrument 200 along one or more circuitous passages, schematically represented as 204. Therefore, the ability to use any one of a plurality of different positioning instruments 200 allows medical personnel to select different positioning instruments having appropriate maneuverability due to their flexibility and/or other physical characteristics to accomplish an efficient disposition of the sleeve 12 relative to an intended dilation site. Accordingly, the positioning instrument 200 may have a variety of shapes and dimensions. For example, the positioning instrument 200 may have a substantially circular cross section. Other cross sectional shapes of the positioning instrument 200 may include, but are not limited to, square, rectangular, cylindrical, hexagonal, or other similar shapes. By way of example only, the sleeve 12 may conform a selected positioning instrument 200 having a substantially circular configuration and a diameter that may range from about 1 millimeter to about 10 millimeters.

Figure 16:
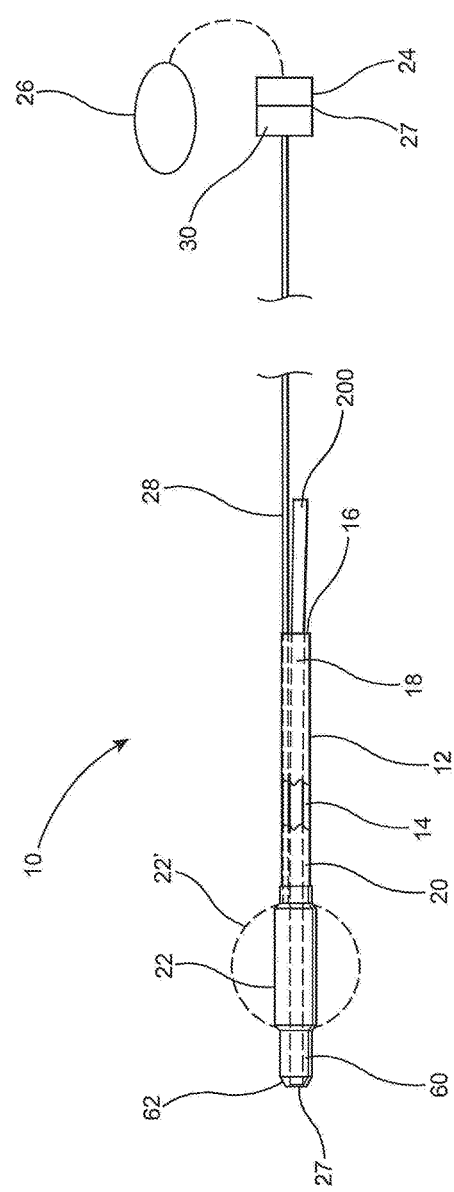
FIG. 16 is a schematic representation of an exterior view of a preferred embodiment of the dilator device according to the present invention similar to but distinguishable from the embodiment as represented in FIG. 11.

In preferred embodiments according to the present invention, the elongated sleeve 12 has a predetermined structural integrity that facilitates positioning the dilator device 10 within the paranasal sinuses 100, such as with a positioning instrument 200 as demonstrated in FIG. 16. Accordingly, the predetermined structural integrity of the elongated sleeve 12 may be defined as the elongated sleeve 12 comprising a preferred rigidity. The preferred rigidity as used herein refers to the elongated sleeve 12 being sufficiently rigid so as to be able to substantially penetrate or move within the paranasal sinuses 100. A preferred rigidity should be such that the sleeve 12 is not excessively rigid so as to cause damage to the paranasal sinuses 100 or so that the sleeve is unable to conform to the paranasal sinuses 100 or the positioning instrument 200. The preferred rigidity may also be defined as the sleeve 12 being sufficiently flexible so that it may at least partially conform to the particular geometry or shape of the paranasal sinuses 100. This predetermined structural integrity of the elongated sleeve 12 may be achieved by providing an elongated sleeve 12 having rigidity values between 10D and 100D as measured on the Shore D Durometer scale. More specifically, the rigidity of the sleeve 12, may fall between values of about 35D and about 72D. Favorable results have been observed with values of about 55D.

Such preferred rigidity values as mentioned above are generally obtained, at least in part, by providing a sleeve 12 having a preferred thickness 70. Accordingly, the thickness 70 of the sleeve 12 should be less than about 0.5 millimeters. Such a thickness 70 facilitates a rigidity of the sleeve 12 that allows for at least partial conformance not only to the positioning instrument 200, but also to the geometry of the paranasal sinuses 100 so that the dilator device 10 may be easily positioned. Favorable results have been observed with a thickness 70 of the sleeve 12 between about 0.10 millimeters and 0.20 millimeters, and more specifically with a thickness of about 0.15 millimeters.

The predetermined structural integrity of the elongated sleeve 12 may be also defined, at least in part, by the materials used to form the elongated sleeve 12. As is represented in the illustrative embodiment of FIG. 13, the elongated sleeve 12 may comprise an outer layer 21 and an inner layer 23. Generally, the outer layer 21 and the inner layer 23 are connected to one another. Additionally, the outer layer 21 is disposed in at least partially enclosing relation to the inner layer 23. Either or both of the outer layer 21 and inner layer 23 may extend along the entire length of the sleeve 12 or part thereof. Alternatively, and as represented in the illustrative embodiment of FIG. 14, the sleeve 12 may comprise only an outer layer 21, and not an inner layer 23. In embodiments comprising both an outer layer 21 and an inner layer 23, the material used to form an outer layer 21 may comprise a thermoplastic elastomer such as, but not limited to, those produced under the brand Vestamid® E and Pebax®. Favorable results have been observed when Pebax® is used to form the outer layer 21. Other materials used to form the outer layer 21 may include a variety of synthetic polymers, such as, but not limited to, nylon, polyurethane, and polyamide. Conversely, the inner layer 23 may be formed by a material comprising polytetrafluoroethylene (PTFE). Other materials may also be used to form the inner layer 23 such as, but not limited to, fluorinated ethylene propylene (FEP), high-density polyethylene (HDPE) or polyethylene high-density (PEHD), and other synthetic polymers such as nylon. Favorable results have been observed by using polytetrafluoroethylene (PTFE) made under the brand Teflon™.

As mentioned above, an alternative embodiment according to the present invention comprises a single outer layer 21. Accordingly, if there is no inner layer 23, a variety of additives may be combined with the material used for the outer layer 21. These materials may include an added lubricant, such as, but not limited to those manufactured under the brand PebaSlix®. Additionally, in embodiments comprising only a single outer layer 21, the material of the outer layer 21 may comprise a thermoplastic elastomer with a polytetrafluoroethylene (PTFE) additive.

The versatility of the sleeve 12 may be further demonstrated by having a sufficient dimension and overall structure which facilitates its use with a positioning instrument 200 incorporating a camera and/or viewing device such as, but not limited to, an endoscope/camera. As a result, the viewing, visual recording, etc. of the paranasal sinuses 100, or other area to be dilated, can be accomplished concurrent to the disposition of the sleeve 12 towards and into an operative orientation relative to the site to be dilated. Moreover, another preferred embodiment of the sleeve 12 is structured to include an open end at the extremity of the distal portion 20. As a result, visual observation and/or a direct communication is established between a selected positioning instrument 200 and an exterior of the distal portion 20, at an outer extremity thereof. This additional preferred embodiment is represented in FIGS. 8-10 and described in greater detail hereinafter.

Moreover, each of a plurality of preferred embodiments of the sleeve 12 includes an expandable and/or inflatable bladder 22 connected to, mounted on or integrally formed with a remainder of the sleeve 12, preferably at the distal portion 20. Moreover, the expandable and/or inflatable bladder 22 may be mounted an exteriorly of the distal portion 20 and normally assume a retracted or non-expanded or non-inflated orientation 22". Alternatively, the expandable and/or inflatable bladder 22 may be mounted interiorly of the distal portion 20 and may similarly assume a retracted or non-expanded or non-inflated orientation 22". In a preferred embodiment, the bladder 22 is integrally formed or otherwise embedded with the remainder of the sleeve 12. However, an operative feature of the sleeve 12 comprises the bladder 22 being capable of expanding and/or being inflated into a radially outward extended or expanded orientation 22'. When in the expanded orientation 22', the bladder 22 preferably extends about the circumference of the sleeve 12 in substantially transversely surrounding relation to a corresponding part of the proximal portion 20. Further, when in its expanded orientation 22', the bladder 22 is further extended radially outward in substantially transverse relation to the length of the sleeve or sheath 12. More specifically, when the bladder 22 is inflated, such as in the expanded orientation 22', the bladder 22 may comprise a diameter that ranges between about 4 millimeters to about 10 millimeters, and more specifically between about 6 millimeters to about 9 millimeters. Favorable results have been observed with a bladder 22 having an inflated diameter of about 7 millimeters.

Figure 11:
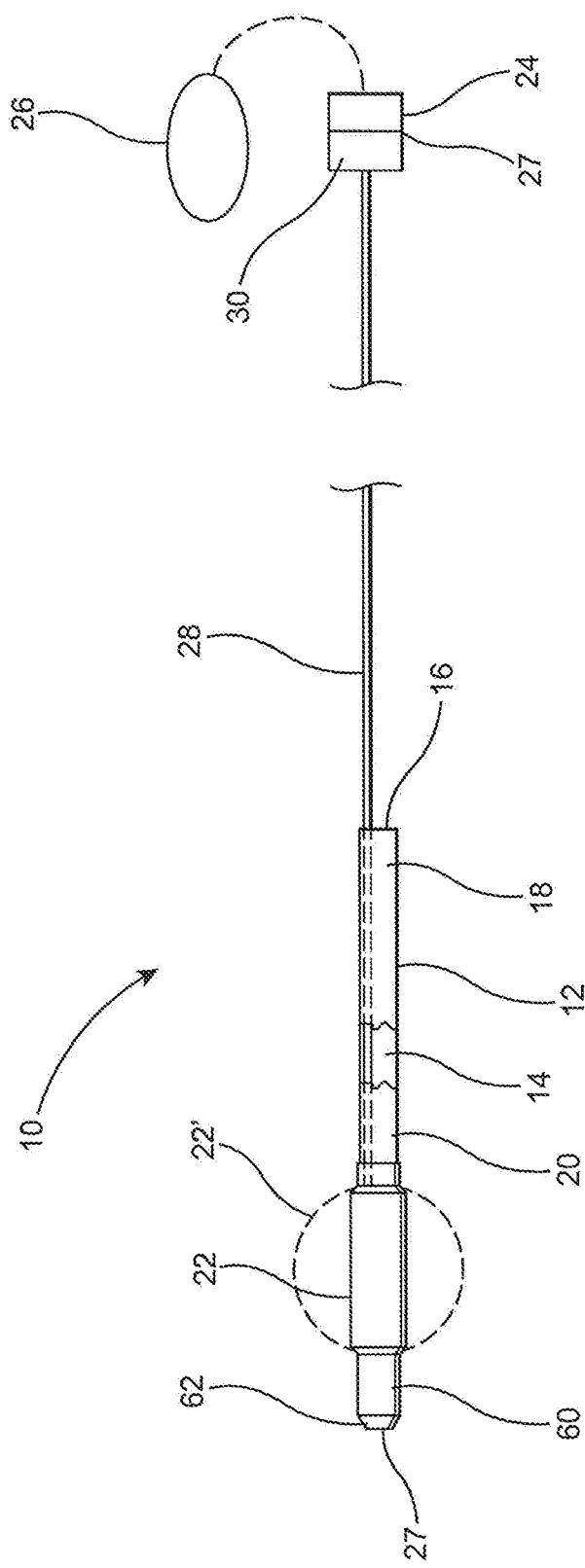
FIG. 11 is a schematic representation of an exterior view of a preferred embodiment of the dilator device according to the present invention comprising a tip with a tapered configuration.
Figure 12:
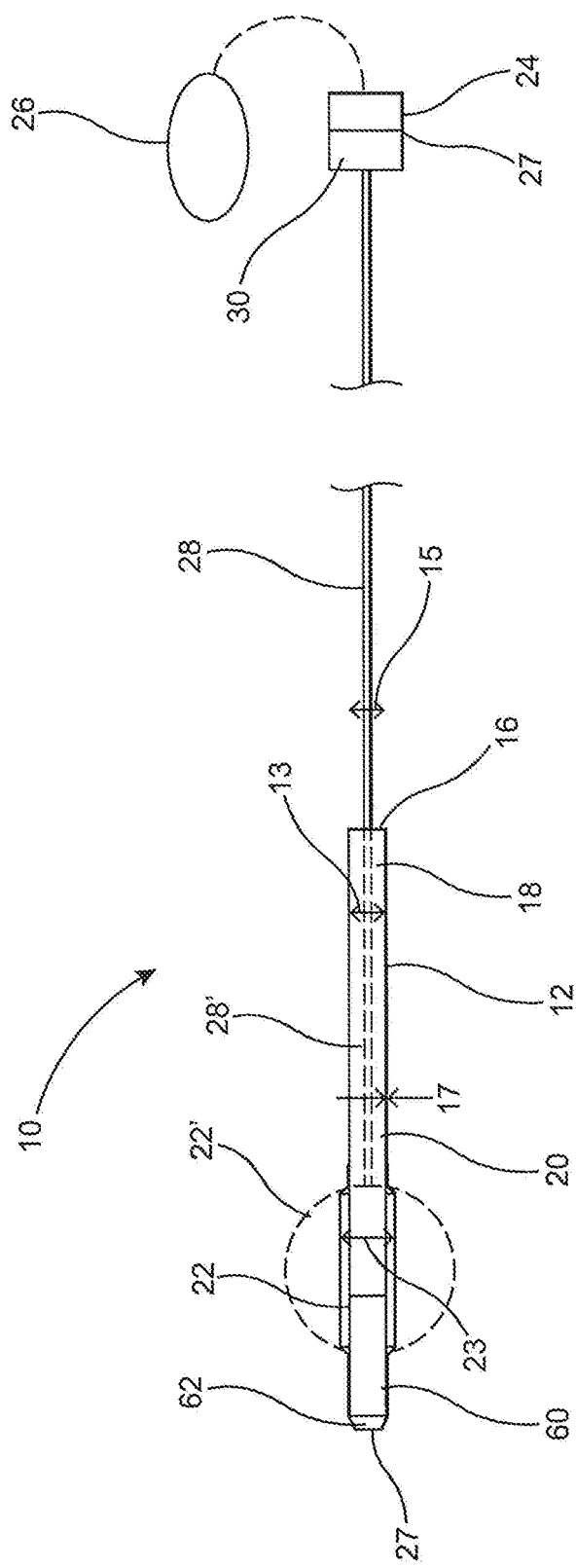
FIG. 12 is a schematic representation of a cross-section of a preferred embodiment of the dilator device according to the present invention comprising a tip with a tapered configuration.
Figure 15:
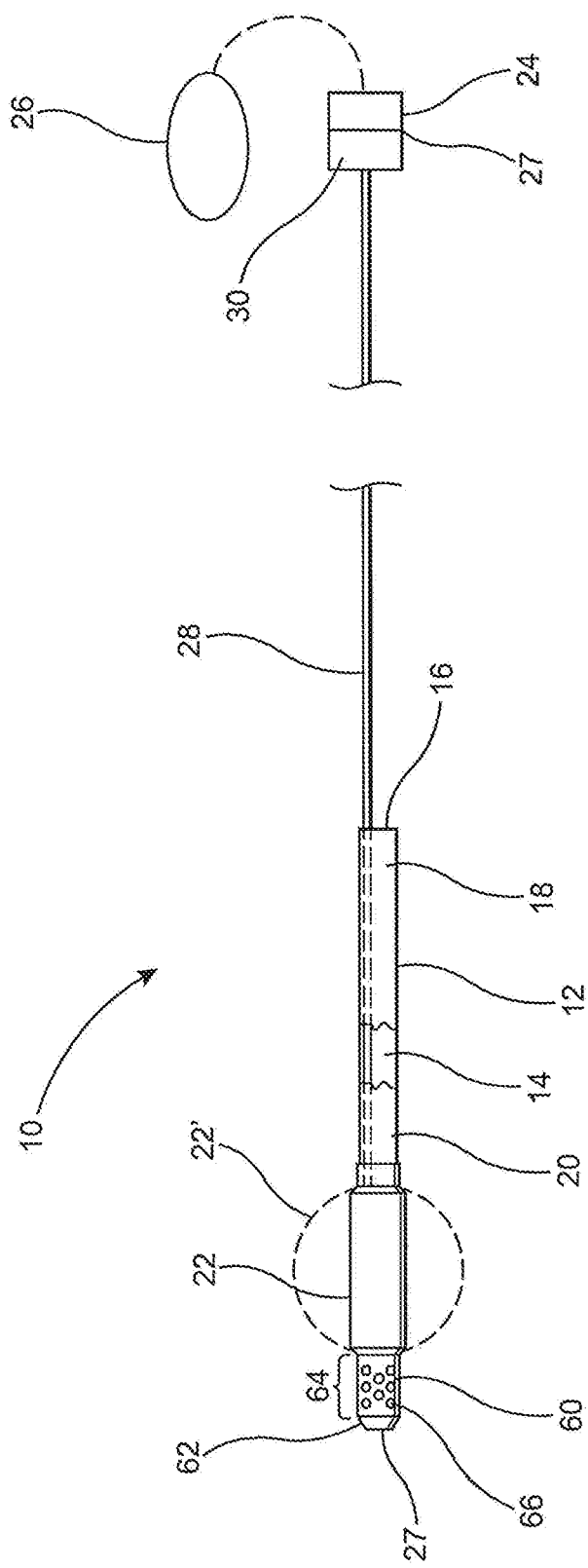
FIG. 15 is a schematic representation of an exterior view of a preferred embodiment of the dilator device according to the present invention comprising a tip with a tapered configuration and a plurality of openings.

Expansion and/or inflation of the bladder 22 is accomplished by the provision of a fluid input generally indicated as 24. Further, fluid input 24 is structured to be removably connected to an appropriate source of fluid 26 such as, but not limited to, it could be a hand manipulated, needleless syringe. However, it is emphasized that the fluid source 26 may assume a variety of different mechanical, electrical, automatic, pre-calibrated and/or hand manipulated devices, which are capable of being removably connected to the fluid input 24. Further, as represented in FIGS. 2 through 7B the versatility of the dilator device 10 of the present invention is enhanced by facilitating the use of any one of a variety of different fluid sources, which are not necessarily an integrated or permanently connected part of the dilator device 10. Therefore, the fluid source 26 is operable to direct a source of fluid such as air, other gas or other fluid through the fluid input 24 and along a fluid flow path which may be in defined at least in part by a conduit 28. As indicated, the flow path or conduit 28 is connected in fluid communication between the fluid input 24 and the interior of the bladder 22. However, as represented in FIGS. 11, 12, and 15 the fluid flow path or conduit 28 does not enter, pass into, or pass through the interior of the bladder 22.

Figure 14:
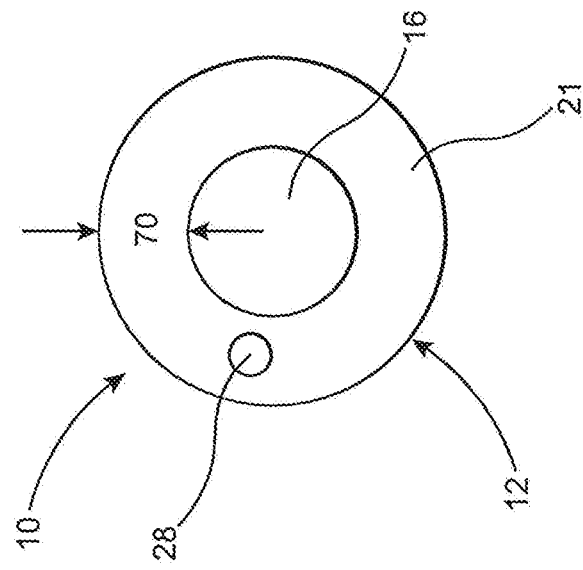
FIG. 14 is a cross-section view of a preferred embodiment of the dilator device according to the present invention comprising an outer layer.
Figure 13:
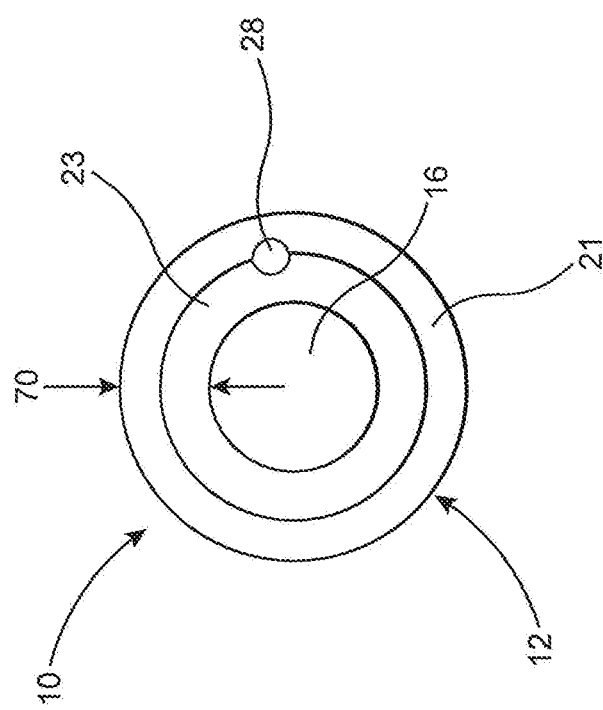
FIG. 13 is a cross-section view of a preferred embodiment of the dilator device according to the present invention comprising an inner layer and an outer layer.

With further reference to the illustrative embodiment as represented in FIG. 13, an enclosing relation of the outer layer 21 relative to the inner layer 23 permits disposition of the conduit 28 between both layers 23 and 21. Alternatively, and as is shown in FIG. 14, the conduit 28 may be disposed substantially within the outer layer 21. This of course differs from the above noted embodiments of FIGS. 2-6, wherein the flow path/conduit 28 is disposed on and passes along the exterior of the sleeve 12 and is connected to the exterior of the bladder 22, in fluid communication with the interior of the bladder 22, without entering or passing through the interior thereof.

As should be apparent certain instances of applying the dilator device 10 in a medical procedure involves the establishment and maintenance of the bladder 22 in the expanded or inflated orientation 22'. Accordingly, the present invention also includes a flow restrictor 30 disposed along and in communication with the fluid flow path or conduit 28. Therefore, maintenance of the bladder 22 in the expanded and/or inflated orientation involves the prevention of fluid leaking from the interior of the bladder 22, when in the expanded/inflated orientation 22'. Accordingly, the flow restrictor 30 is disposed and structured to restrict fluid flow in at least one direction, schematically represented as 28' in FIGS. 7A and 7B, from the interior of the bladder 22 to an exterior thereof and/or to an exterior of the sleeve or sheath 12.

Figure 7A:
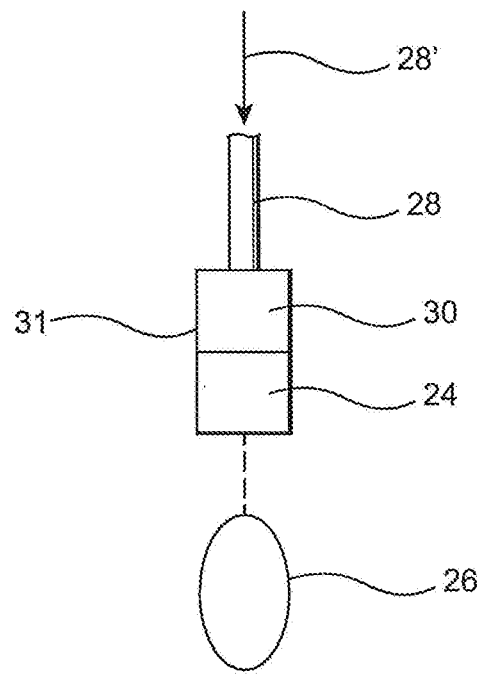
FIG. 7A is a schematic representation in partial cutaway of a fluid input device which may be operatively associated with the embodiments of FIGS. 1-6.
Figure 7B:
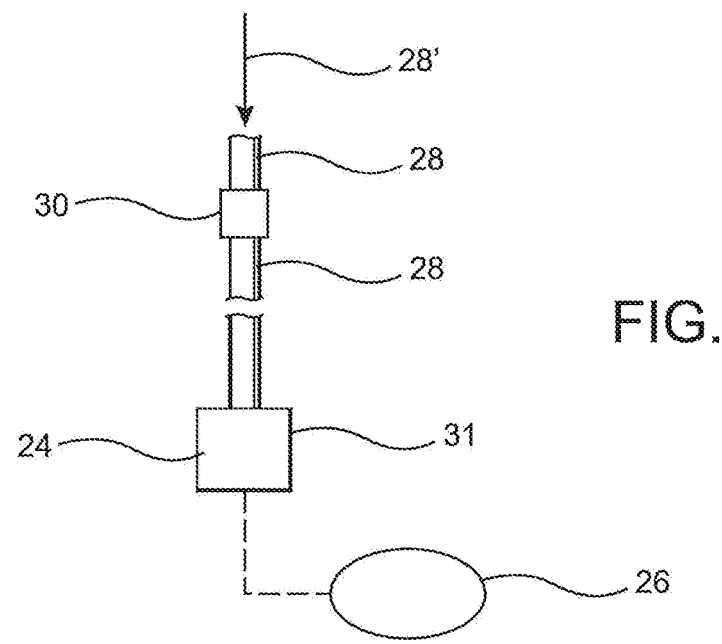
FIG. 7B is a schematic representation in partial cutaway of yet another embodiment of a fluid input device which may be operatively associated with the embodiments of FIGS. 1-6.

With further reference to FIGS. 7A and 7B, different embodiments of the fluid input 24 includes it being connected to or otherwise operatively associated with the flow restrictor 30, such as by being encased within a common housing or the like 31 (renumber and change drawings. In contrast, and for the reasons set forth in greater detail hereinafter, the flow restrictor 30 may be located in spaced relation to the fluid input 24 and along the fluid flow path or conduit 28, as schematically represented in FIGS. 5, 6 and 7B. As such, the flow restrictor 30 may be located at any point along and in operative association with the flow path at least partially defined by the fluid conduit 28, so as to restrict fluid flow from the interior of the bladder 22, once it is in its expanded and/or inflated orientation 22'. Further, as also represented in FIGS. 7A and 7B the flow restrictor 30 may be in the form of a check valve which is normally operable to restrict fluid flow along the fluid flow path in at least a first direction 28' between the bladder 22 and the fluid input 24.

During normal usage it will of course be necessary to remove the sleeve 12 of the dilator device 10 from its operative position relative to an inflation site, such as associated with the paranasal sinuses 100. In doing so, the bladder 22 will be selectively deflated or reduced from its expanded orientation 22' into its normal, non-inflated, non-expanded and/or retracted orientation 22". Accordingly, the flow restrictor 30, which may include a one-way check valve or similarly operative structure, is structurally operative to selectively allow fluid flow in the direction 28' schematically represented in FIGS. 7A and 7B, from the interior of the bladder 22 through an appropriate portion or length of the fluid flow conduit 28 to an exterior of the sleeve or sheath 12. As also described in greater detail hereinafter the exiting of the fluid in the initially restricted first direction 28' may be directed through the fluid input 24 or exit from another portion of the fluid conduit 28 to an exterior of the sleeve 12, when it is desired to deflate or retract the bladder 22.

With primary reference to FIGS. 5 and 6, one or more additional preferred embodiments of the dilator device 10 includes the proximal portion 18 being separable and disconnected from the distal portion 20. Such situations may commonly arise when the bladder 22 is intended to be maintained in an operative position relative to a dilation site for an extended period of time, while in the inflated or expanded orientation 22'. Accordingly one feature of the dilator device 10 includes its ability to be used with any of a plurality of positioning instruments 200 which may be easily, quickly and simply removed from the interior 14 of the sleeve 12 once it is disposed at the dilation site and expanded or inflated. Further, when intended to be retained for an extended time, it may be desirable to reduce the overall length of the sleeve 12. Such reduction in the length may be accomplished by separating the distal portion 18 from the distal portion 20 along a frangible portion 40. As such, the frangible portion 40 preferably includes a weakened segment or segmented seem which facilitates the disconnection and/or separation of the proximal portion 18 from the distal portion 20. Further, such separation may easily occur when a sufficient pulling or other appropriately directed force is applied to the proximal portion 18. Further, the weakened segmented structuring of the frangible portion or seam 40 is structured to break away or cause the intended separation by an exerted force, which is insufficient to dislodge the bladder 22, when in its expanded or inflated orientation 22', from the dilation site. In addition, the present invention contemplates that the frangible portion 40 preferably extends circumferentially around the entire sleeve 12 or at least a majority thereof. Also, the frangible portion may be structured to break away or facilitate separation between the proximal and distal portions 18 and 20 using the appropriate instrumentation instead of the aforementioned pulling or appropriately directed force.

As also noted from a review of FIGS. 5 and 6, the frangible portion 40 may be located at various positions along the length of the sleeve 12, dependent upon the particular dilation procedure intended. Accordingly, when the frangible portion 20 is located closer to the access opening 16, the distal portion 20 may include a tail portion 20'. The tail portion 20' may be of sufficient length to be accessible from within or from without the paranasal sinuses 100 or other location of the dilation site. This accessibility due to the somewhat elongated dimension of the tail portion 20' facilitates the subsequent removal of the distal portion 20 from the intended dilation site, using instrumentation or merely exerting a sufficient pulling force thereon, will once the bladder 22 is deflated into its retracted orientation 22".

It should be apparent that when the proximal portion 18 is separated and/or disconnected from the distal portion 20 it still may be important to maintain the bladder 22 in the expanded or inflated orientation 22'. Accordingly the aforementioned flow restrictor 30 may be mounted on or connected to the distal portion 20 in flow regulating relation to a corresponding portion of the flow path or conduit 28, regardless of the location of the frangible portion 40 as demonstrated FIGS. 5 and 6. Moreover, the flow restrictor 30, regardless of its location, should still be accessible either by hand or through appropriate instrumentation so as to allow fluid flow to pass in the direction 28' thereby allowing the deflation of the bladder 22 from its expanded or inflated orientation 22' into its retracted orientation 22". Therefore, while the flow restrictor 30 is normally structured to restrict fluid flow in the direction 28', it is also structured to selectively allow fluid flow in the direction 28' in order to facilitate the deflation of the bladder 22 into its normal retracted or collapsed orientation 22".

As set forth above, yet another preferred embodiment of the dilator device 10 is represented in FIGS. 8A-10. More specifically, this preferred embodiment of the dilator device 10 includes an elongated sleeve represented as 12'. The elongated, flexible material sleeve 12' includes the aforementioned access opening 16 at the outer extremity of the proximal portion 18 and also an open end 27 at the outer extremity of the distal portion 20. As also represented, the access opening 16 and the open end 27 are substantially oppositely disposed by virtue of their corresponding position relative to the opposite, outer extremities of the proximal portion 18 and the distal portion 20. The open end 27 facilitates a corresponding outer or distal end 210 of the selected positioning instrument 200 being disposed in direct, open, viewing relation and/or fluid communication to the area intended to be dilated such as, but not limited to the paranasal sinuses 100. For purposes of clarity, the term "direct viewing relation", "direct fluid communication" and/or "direct access" is meant to include the end 210 and any device associated there with being openly exposed to the area being dilated, rather than being positioned adjacent thereto but separated therefrom by a closed end 25 of the sleeve 12, as generally represented in FIGS. 2-6.

As further represented in FIGS. 9 and 10 the positioning instrument 200 may include an appropriate connector 12 which facilitates the removable attachment of the positioning instrument 200 to a negative pressure source. As a result the paranasal sinuses 100 or other area to be dilated can be suctioned continuously or selectively as the dilator device moves into and is disposed at an operative orientation relative to the site being dilated.

In addition, the positioning instrument 200 may include a viewing device, and/or endoscope/camera located on or adjacent to the end 210 or other appropriate location on the selected positioning instrument 200. As such, the viewing device, camera, etc. and the end 210 will be disposed, when assembled with the dilator device 10 as represented in FIG. 10, asked or in corresponding relation to the open end 27 to facilitate direct access and communication with the area to be dilated. Such direct access will allow a direct viewing or other type communicating relation of the end 210 and/or device associated therewith, with the area to be dilated through the open end 27. Moreover, such direct access or direct communication will enable real-time viewing, recording, and/or other type of visual observation of the area being dilated such as, but not limited to, the paranasal sinuses 100.

By way of example only, the represented positioning instrument 200 may be formed of an appropriate material and be cooperatively dimensioned with the sleeve 12' to be disposed telescopically within the interior thereof as schematically represented by directional arrow 29. Accordingly, when in the assembled form as represented in FIG. 10, the end or viewing device, camera, etc. 10 will be disposed adjacent and/or corresponding position relative to the open end 27 thereby allowing the aforementioned direct access and/or communication. As indicated the direct communication will facilitate the performance of suctioning and/or direct viewing of the area to be dilated during the positioning and final intended location of the bladder 22 in the operative orientation relative to a specific site to be dilated.

As represented in FIGS. 11 and 12, additional features of the present invention include providing a sleeve 12 that comprises a tip 60 having a predetermined configuration that facilitates positioning the dilator device 10, and more specifically the elongated sleeve 12, within the paranasal sinuses 100. Accordingly, the predetermined configuration may be defined as the tip 60 having a substantially tapered configuration, indicated as 62 in FIGS. 11, 12, 15 and 16. The tapered configuration 62 should be such that the sleeve 12, and more specifically the tip 60, similarly comprises an open end 27. The tapered configuration 62 of the tip 60 also facilitates entry of the sleeve 12 and bladder 22 into relatively small openings, such as within the paranasal sinuses 100. The tapered configuration 62 reduces the effective diameter of the tip 60 so that the open end 27 may reach smaller openings than otherwise without a tapered configuration 62. Furthermore, the tapered configuration 62 also serves to more effectively direct the tip 60, and consequently the sleeve 22, towards a desired location within the paranasal sinuses 100.

Figure 3:
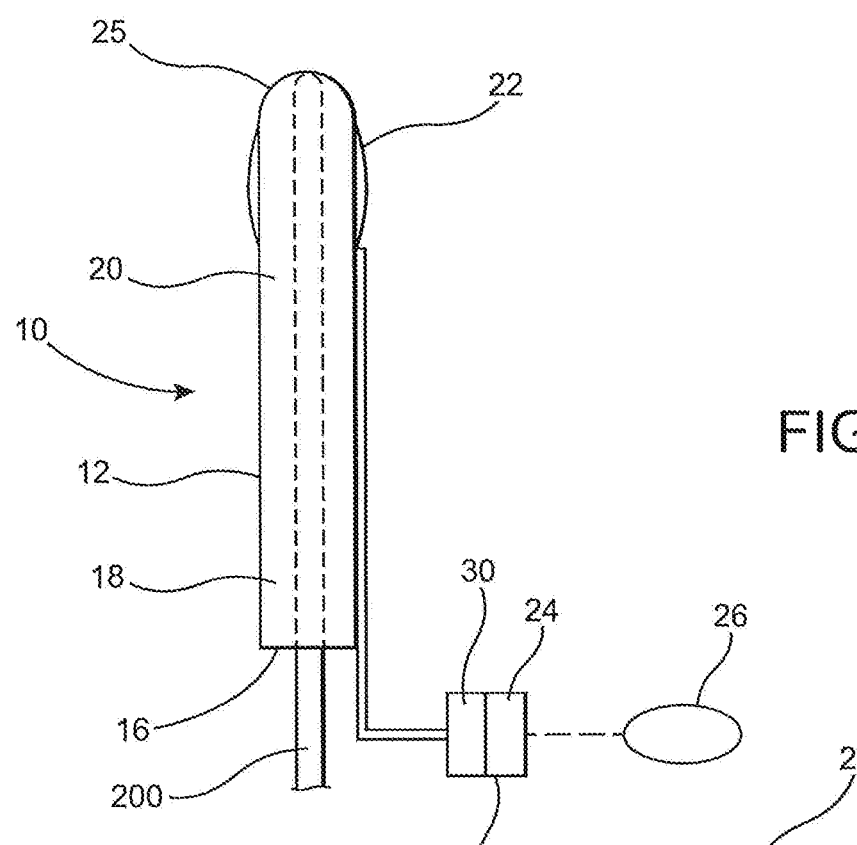
FIG. 3 is a schematic representation of the embodiment of FIG. 2 in an expanded orientation.
Figure 4:
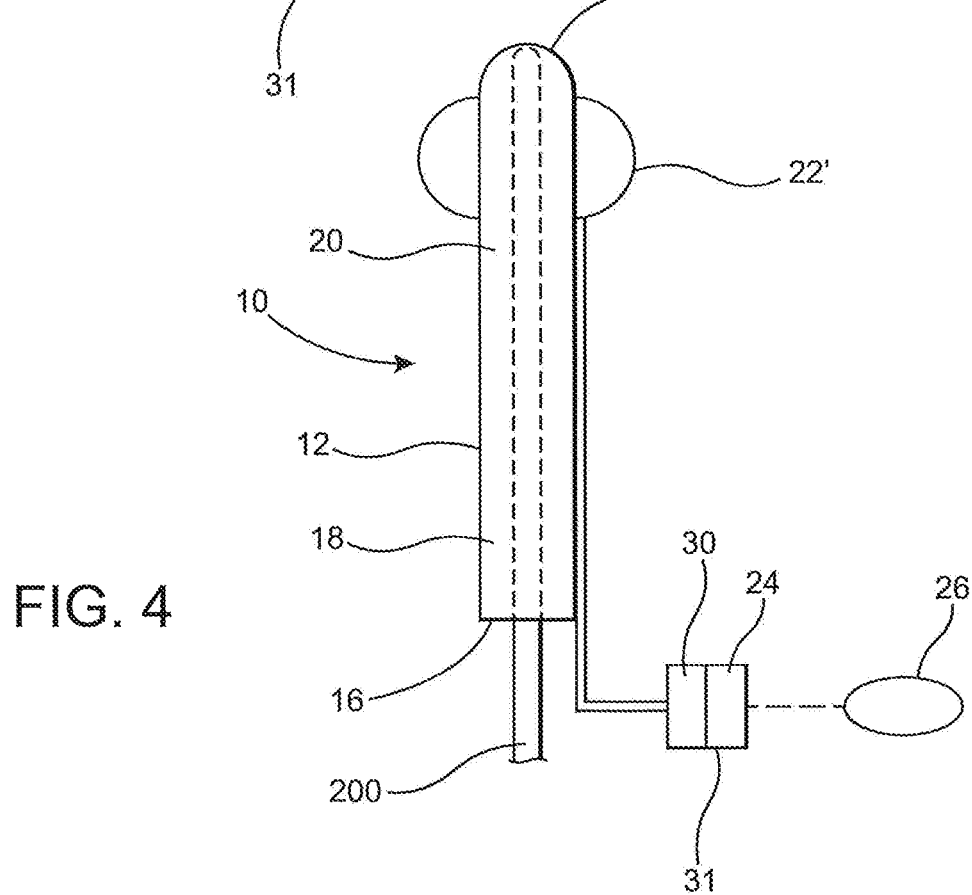
FIG. 4 is a schematic representation of yet another embodiment of a dilator device of the present invention operatively similar to but distinguishable from the embodiments of FIGS. 1-3.

Similar to the embodiments of FIGS. 3 and 4, as described above, and as also represented at least in FIG. 16, a positioning instrument 200 may be inserted through the access opening 16 and disposed substantially along the length of the sleeve 12 on the hollow interior 14. As can be appreciated in FIG. 16, the size of the open end 27 should be smaller relative to the size of the positioning instrument 200 to prevent further movement of the positioning instrument 200 beyond the open end 27. As shown in FIG. 16, the positioning instrument 200 may be disposed against or may be in direct contact with at least a portion of an inside of the tip 60, and more specifically an inside of the tip 60 around its tapered configuration 62. Consequently, when the positioning instrument 200 is disposed against an inside of the tip 60 around the tapered configuration 62, further movement of the positioning instrument 200 results in a substantially corresponding movement of the elongated sleeve 12, and consequently the dilator device 10.

The dilator device 10 of the present invention may be used not only to dilate various parts of the body, such as the paranasal sinuses 100, but may also be used to facilitate suction of an intended location. As previously mentioned, the dilator device 10 of the present invention may be used in conjunction with a suction component, or other instrument that can exert negative pressure to an intended location. When the dilator device 10 is used in conjunction with a suction component, there may be instances where it may be desirable to adjust the position of the dilator device 10 while maintaining the suction component in a fixed position. Similarly, it may be necessary to adjust the position of the suction component while maintaining the bladder 22 in a fixed position. For example, once the bladder 22 is positioned over a desired area, it may be desirable to move the suction component beyond the open end 27 in order to treat a deeper location within paranasal sinuses 100. Also as an example, once the suction component is positioned at a desired location, it may be necessary to move the bladder 22 to expand a different area within the paranasal sinuses 100. Accordingly, both the suction component and the sleeve 12 should be dimensioned and configured to establish a movable and sliding relation between them. In order to achieve this, the size of the hollow interior 14 should be sufficient so as to receive therein the suction component. Additionally, the size of the open end 27 should be such that the suction component may reciprocally move within the hollow interior 14, and so that it may also pass through the open end 27.

The suction component may be disposed in an "operative condition" that may be defined as the suction component being operative to exert negative pressure at or around the intended body part. The "operative condition" may occur concurrent to or independently of movement of the suction component and sleeve 12 relative to each other. Furthermore, the predetermined configuration of the tip 62 may also comprise the open end 27 and the hollow interior 14 being disposed in fluid communication with the suction component. If so desired, a fluid communication as described above, enables the sleeve 12 exert negative pressure at or around an intended body part. Thus, the sleeve 12 may effectively act as an extension to the suction component. Moreover, and although not necessarily required, the positioning instrument 200 may comprise a suction component. That is, the suction instrument 200 may be structured to operate with a suction component. Alternatively, the suction instrument 200 may comprise an integrally formed suction component. Thus, a positioning instrument 200 comprising a suction component may be disposed in fluid communication with the hollow interior 14 to enable the sleeve 12 to exert negative pressure at or around an intended body part.

Yet additional features of the present invention comprise navigation capabilities. The elongated sleeve 12, and more specifically the tip 60, may be configured to enable a navigation interface. A navigation interface as used herein may be at least partially defined as an external device that can be located on the exterior of the body and configured to substantially duplicate the movement of the dilator device 10, such as when the dilator device 10 is located within the paranasal sinuses area 100. More specifically, the external device may be located on the exterior of the body, such as on the skin of the face of a person, but in substantial alignment with paranasal sinuses 100 and dilator device 10 located therein. The external device may form an at least partially operable magnetic interface with the tip 60. In order to achieve a magnetic interface, the external device should comprise a magnet while the tip 60 should comprise a material capable of being attracted to a magnet. Alternatively, the tip 60 may comprise a magnet, while the external device may comprise a material capable of being attracted to a magnet. Materials suitable to form a magnetic interface include, but are not limited to, iron, nickel, and cobalt. Thus, when the dilator device 10 moves or penetrates within the paranasal sinuses 100, the magnetic interface will permit the external device to substantially duplicate the movement of the dilator device 10. Therefore, the external device may move on or relative to the face of the person according to the movement 100 of the dilator device 10, and more specifically the tip 60, within the paranasal sinus area 100. Such a substantially duplicative movement of the external device may thus be used to determine at least an approximate position and preferably a reliably accurate position of the tip 60 within the paranasal sinuses 100.

The navigation interface may also be at least partially defined as a component of the tip 60 that is observable on a variety of imaging capabilities such as, but not limited to, x-rays, MRIs, and CT or CAT scans. For example, this observable component may be a material such as, but not limited to, barium sulfate which may act as a contrast agent that is observable on an x-ray. Thus, the tip 60 may be configured to include such an observable component so that the movement of the dilator device 10 may be tracked as it penetrates the paranasal sinuses 100. Further as an example, one or more x-rays of the intended area may be taken to track and determine the specific location of the dilator device 10 when located within the paranasal sinuses 100.

As represented in FIG. 15, even more additional features of the dilator device 10 of the present invention comprise an irrigation structure configured to provide irrigation to an intended body part. Accordingly, the sleeve 12, and more specifically the tip 60, may comprise an irrigation portion, indicated as 64. The tip 60, and more specifically the irrigation portion 64, may comprise one or more irrigation openings, such as at 66, which may be used to irrigate the intended body part. The interior of the tip 60 and the irrigation opening(s) 66 should be disposed in fluid communication with at least a portion the hollow interior 14 so that a fluid may pass through the hollow interior 14 and exit through the irrigation opening(s) 66 to irrigate the intended body part. The irrigation fluid may come from a second or different source than the fluid source 26 that inflates the balloon. Alternatively, the irrigation fluid may come from the same fluid source 26.

The irrigation mechanism of the dilator device 10 can function independently or in conjunction with a suction component being disposed in the "operative condition." Accordingly, suction and irrigation do not need to occur concurrently, but may occur concurrently if so desired. Moreover, suction and/or irrigation may occur with or without the bladder 22 being in the expanded orientation 22'. Therefore, the dilator device 10 of the present invention is sufficiently versatile such that positioning of the dilator device 10 within the paranasal sinuses 100, inflation of the bladder 22, suction, a navigation interface, and irrigation of the paranasal sinuses 100, are all functions that may occur independently or concurrently, depending on the need.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method for treating sinusitis, the method comprising:
    inserting a positioning element into a dilation device comprising an elongated sleeve sequentially through an access opening disposed on a proximal portion of a hollow interior extending along a length of the elongated sleeve to a tip disposed on a distal portion of the elongated sleeve,
        wherein the distal portion of the elongated sleeve comprises a bladder extendable outwardly in an expanded orientation,
        wherein the bladder is in fluid communication with a fluid input;
    positioning the positioning element disposed within the dilation device to an opening in a paranasal sinus; and
    expanding the bladder in to the opening in the paranasal sinus with a fluid through the fluid input.

2. The method of claim 1, further comprising:
    navigating the dilation device with a navigation interface comprising a component disposed on the tip and structured to at least partially define a magnetic interface with an external device.

3. The method of claim 2, wherein the navigation interface comprises a component disposed on the tip and comprising a material observable on at least one imaging device.

4. The method of claim 3, wherein the material of the component is formulated to be observable on an x-ray.

5. The method of claim 1, further comprising suctioning material from the opening in the paranasal sinus.

6. The method of claim 1,
    wherein the tip comprises an open end configuration to facilitate connecting the positioning element with the elongated device, the tip configured to facilitates positioning of the dilation device, the tip in communicating relation with the hollow interior,
    wherein the open end configuration and the hollow interior configured and dimensioned to permit movement of the elongated sleeve and a suction component relative to one another.

7. The method of claim 1, wherein the tip comprises a taper.

8. The method of claim 1, further comprising irrigating via the tip the paranasal sinus, wherein the tip comprises an irrigation structure disposed in fluid communicating relation between the hollow interior and an exterior of the tip.

9. The method of claim 8, wherein the irrigation structure comprises at least one irrigation opening disposed on the tip.

10. The method of claim 9, wherein the irrigation structure comprises an irrigation portion disposed between the tip and the bladder, the irrigation portion segregated from the tip and the bladder, the at least one irrigation opening disposed along the irrigation portion.

11. The method of claim 1, further comprising:
    irrigating the paranasal sinus with an irrigation structure; and
    suctioning material from the opening in the paranasal sinus with a suction component.

12. The method of claim 1, wherein the tip comprises a tapered configuration.

13. The method of claim 1, wherein the access opening and the hollow interior are structured and dimensioned to removably receive therein the positioning element.

14. The method of claim 1, wherein the fluid input comprises a conduit integrated at least partially into the elongated sleeve.

15. The method of claim 1, wherein the elongated sleeve comprises a flexibility that facilitates positioning the elongated sleeve within the opening in the paranasal sinus.

16. The method of claim 1, wherein the elongated sleeve comprises an outer layer and an inner layer connected to one another and extending along a length of the hollow interior, the outer layer disposed in at least partially enclosing relation to the inner layer.

17. The method of claim 1, wherein the elongated sleeve comprises a material selected from the group consisting of a nylon, a polyurethane, and a poly amide.

18. The method of claim 1, further comprising suctioning a material from the opening in the paranasal sinus via an open end formed on the tip and disposed in communicating relation with the hollow interior.

19. The method of claim 1, wherein the dilation device further comprises a thermoplastic elastomer.

* * * * *